United States Patent [19]

Schulze et al.

[11] 4,315,866
[45] Feb. 16, 1982

[54] PROCESS FOR PREPARING 11-KETO STEROIDS

[75] Inventors: Paul-Eberhard Schulze; Ulrich Kerb, both of Berlin, Fed. Rep. of Germany

[73] Assignee: Schering, A.G., Berlin, Fed. Rep. of Germany

[21] Appl. No.: 215,761

[22] Filed: Dec. 10, 1980

[30] Foreign Application Priority Data

Dec. 10, 1979 [DE] Fed. Rep. of Germany ....... 2950026

[51] Int. Cl.$^3$ ............................................. C07J 5/00
[52] U.S. Cl. ............................ 260/397.3; 260/397.45
[58] Field of Search ................................... 260/397.45

[56] References Cited

FOREIGN PATENT DOCUMENTS 2817081 11/1975 Fed. Rep. of Germany ... 260/397.3

OTHER PUBLICATIONS

Chemical Abstracts (1970), vol. 73, Pars. 25730h.
Fieser and Fieser, "Steroids", 1961, 743.

*Primary Examiner*—Elbert L. Roberts
*Attorney, Agent, or Firm*—Millen & White

[57] ABSTRACT

A process for preparing an 11-keto steroid consists essentially of heating the corresponding 9α-halo-11β-hydroxy steroid, to 180°–350° C. in an inert, aprotic, high-boiling solvent.

7 Claims, No Drawings

PROCESS FOR PREPARING 11-KETO STEROIDS

BACKGROUND OF THE INVENTION

The present invention relates to a new process for preparing 11-keto steroids.

According to conventional methods, 11-keto steroids are obtained from the corresponding $\Delta^{9(11)}$-steroids, by first forming the bromohydrin with hypobromous acid, then removing the 9α-bromine reductively with tributyltin hydride, for example, and finally oxidizing the 11β-hydroxy compound to the 11-keto compound. The conventional chemical methods, however, are disadvantageous in that they either proceed via several stages or produce unsatisfactory yields.

SUMMARY OF THE INVENTION

Accordingly, it is an object of this invention to provide a new process of preparing 11-keto steriods which, inter alia, is simpler than the conventional methods and enables higher yields.

Upon further study of the specification and appended claims, further objects and advantages of this invention will become apparent to those skilled in the art.

These objects have been attained by this invention by providing a process for preparing an 11-keto steroid consisting essentially of heating the corresponding 9α-halo-11-βhydroxy steroid to 180°–350° C. in an inert, aprotic, high-boiling solvent.

DETAILED DISCUSSION

Halogen includes chlorine and bromine.

The compounds producible according to the process of this invention are either per se conventional, biologically active compounds or they serve as conventional intermediates for the production of such compounds. For example, 11-keto-5α-pregnanes and the D-homo-analogs thereof are known to be i.v. anesthetics; and it is possible to prepare cortisone and other corticoids by side chain buildup from the corresponding 4-androstene-3,11, 17-trione.

The reaction of this invention is surprising since it would have been expected that, during heating to temperatures above the melting point of the respective compounds, thermal decompositions and rearrangements would occur. Also, a quite different reaction per se would have been expected. For example, when heating 9α-chloro-11β-hydroxy-$\Delta^{1,4}$-3-keto steriods in the presence of potassium acetate or potassium carbonate, the corresponding 9β,11β-epoxy-$\Delta^{1,4}$-3-keto steroids are obtained (Fieser and Fieser, "Steroids," 1961: 743). Alternatively, the $\Delta^9$-11-hydroxy steroids are obtained when heating in collidine or pyridine (DOS [German Unexamined Laid-Open Application] 2,817,081). However, sterically uniform compounds are obtained by the process of this invention which is carried out without the presence of such reagents.

The 9α-halogen-11β-hydroxy steroids used as starting materials can be further substituted to form equivalent steroids. Examples of suitable substituents include lower alkyl groups, such as methyl, in the 2-, 6-, 16-, 18-, and 21-positions, and hydroxy in the 3-position. Another halogen atom, such as fluorine or chlorine can be present in the 6-position. Alkynyl groups, such as the ethynyl group in the 17-position, and keto groups in the 3- and 20-positions can be present as well. A methylene group can be in the 1,2- and/or 6,7-position. Double bonds can be in the 1-, 4-, 5- and/or 6-position. Acyloxy groups can be in the 3-and/or 21-position. The process of this invention is also not restricted to steroids of the cyclopentanophenanthrene series. The process is also applicable to steroids of the D-homo series.

If an acylated hydroxy group is present in the 17α-position, this group can be split off under the reaction conditions of this invention, forming a $\Delta^{16}$-double bond.

The process of this invention is conducted by dissolving the starting material in the proper solvent and heating the solution to temperatures of 180°–350° C., preferably 200°–300° C., for a period of 3–20 minutes.

Suitable solvents include inert, high-boiling (e.g., b.p.'s of at least 150°–200° C.) aprotic solvents, e.g. biphenyl, diphenylene oxide, dibenzylbenzene, oligoglycol dimethyl ethers, such as di-, tri-, and polyglycol 200 dimethyl ethers, as well as poly-$C_{4-8}$-alkanediol dimethyl ethers, and mixtures thereof with one another. These liquids are, in part, commercially available. Under the name of "Dowtherm" A, a eutectic mixture of biphenyl and dibenzofuran (b.p. approximately 285° C.) is available; under the name of "Marlotherm" S, it is possible to obtain dibenzylbenzene isomeric mixtures (b.p. approximately 390° C.); and under the designation "polyglycol 200 dimethyl ether", there is available a mixture of homologs of pentaethylene glycol dimethyl ether, $CH_3O(CH_2CH_2O)_nCH_3$, n=2–10 (boiling point range 240°–350° C.).

The solvent is employed in an amount of 2–50 parts by weight, preferably 5–20 parts by weight, based on the quantity of starting material.

The reaction can be conducted under atmospheric pressure. Reduced pressure is recommended when working with heat-sensitive substances, such as, for example, $\Delta^{1,4}$-steroids having a halogen atom in the 6-position. The practical pressure usually ranges from 1 to 30 mm Hg.

It is advantageous to heat the reaction mixture under a protective gas atmosphere, such as nitrogen, for example, in order to exclude the effects of oxygen. It is also advantageous to introduce the compound into the solvent in the solid form under a protective gas, the solvent having previously been brought to the desired temperature. The course of the thermolysis can be readily controlled by thin-layer chromatography. After the reaction has been terminated, the reaction mixture is cooled and worked up as usual such as by filtration, washing, and elution. A preferred working-up procedure is the removal of the solvent by steam distillation, drying of the residue, and recrystallization.

From a general point of view, the process of this invention has the advantage that it involves an exceedingly simple manipulation. The compound is simply heated in the solvent and then again separated from the solvent after the reaction. Another advantage of the process is that any split-off hydrogen halide and/or readily volatile organic acids, such as acetic or propionic acid, escape from the reaction medium during heating. Neutralization is unnecessary. Acid catalyzed rearrangements, such as, for example, the dienone phenol rearrangement of $\Delta^{1,4}$-3-keto steroids, cannot even occur. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

One gram of 9α-chloro-11β-hydroxy-16α-methyl-21-trimethylacetoxy-1,4-pregnadiene-3,20-dione is stirred in 4 ml of "Marlotherm" S for 5 minutes at an oil bath temperature of 300° C. under argon. After cooling, the mixture is diluted with toluene and chromatographed on silica gel, thus obtaining 650 mg of 16α-methyl-21-trimethylacetoxy-1,4-pregnadiene-3,11,20-trione; mp 201°–202.5° C. (acetone-hexane).

EXAMPLE 2

Under argon, 3 g of 9α-chloro-11β-hydroxy-16α-methyl-21-trimethylacetoxy-1,4-pregnadiene-3,20-dione is stirred in 10 ml of polyglycol 200 dimethyl ether (boiling range 240°–350° C.) for 8 minutes at an oil bath temperature of 300° C. After cooling, the mixture is poured into 200 ml of ice water; the precipitated product is vacuum-filtered and dried, and recrystallization from acetone-hexane yields 1.4 g of 16α-methyl-21-trimethylacetoxy-1,4-pregnadiene-3,11,20-trione, which is identical to the compound prepared in accordance with Example 1.

EXAMPLE 3

Under agitation and introduction of gaseous nitrogen, 1 g of 9α-chloro-17α,21-dipropionyloxy-11β-hydroxy-16β-methyl-1,4-pregnadiene-3,20-dione is added in the solid form to 10 ml of "Marlotherm" preheated to 280° C. The temperature is maintained for 4 minutes and then the mixture is allowed to cool. The solution is chromatographed on silica gel. With hexane, the "Marlotherm" is eluted first of all, and then the mixture is chromatographed with hexane-ethyl acetate (0–30%), thus obtaining 730 mg of 16β-methyl-21-propionyloxy-1,4,16-pregnatriene-3,11,20-trione (92% of theory); mp 173°–178° C.

UV: $\epsilon_{243} = 19600$.

EXAMPLE 4

Under argon gas, 1 g of 9α-bromo-11β-hydroxy-4-androstene-3,17-dione is agitated in 5 ml of "Dowtherm" A for 3 minutes at 250° C. To work up the reaction mixture, the solvent is removed by steam distillation, the residue is dried and recrystallized from methylene chloride-isopropyl ether, thus obtaining 635 mg of 4-androstene-3,11,17-trione, mp 214°–216° C.

EXAMPLE 5

Analogously to Example 4, using as the starting compound 9α-bromo-3α-acetoxy-11β-hydroxy-5α-pregnan-20-one, 3α-acetoxy-5α-pregnane-11,20-dione, mp 143°–145° C. (85% of theory) is obtained; and using 9α-bromo-3α-acetoxy-11β-hydroxy-D-homo-5α-pregnan-20-one as the starting material, 3α-acetoxy-D-homo-5α-pregnane-11,20-dione, mp 182.5°–183.5° C. (90% of theory) is produced.

EXAMPLE 6

1.5 g of 9α-bromo-6α-fluoro-11β-hydroxy-16α-methyl-21-trimethylacetoxy-1,4-pregnadiene-3,20-dione is introduced at 220° C. into 20 ml of "Marlotherm" S and heated to boiling for 15 minutes under a vacuum of 19 mm Hg [$bp_{19} = 242°$ C.]. After cooling, the mixture is diluted with methylene chloride and chromatographed on silica gel, thus obtaining 920 mg of 6α-fluoro-16α-methyl-21-trimethylacetoxy-1,4-pregnadiene-3,11,20-trione, mp 226°–227° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an 11-keto steroid consisting essentially of heating the corresponding 9α- halo-11β-hydroxy steriod to 180°–350° C. in an inert, aprotic, high-boiling solvent.
2. A process of claim 1 wherein the heating temperature is 200°–300° C.
3. A process of claim 1 wherein halo is chlorine or bromine.
4. A process of claim 1 wherein the amount of solvent is 2–50 wt. parts per wt. part of starting steroid.
5. A process of claim 1 wherein the reaction is conducted under a protective gas atmosphere.
6. A process of claim 1 wherein the starting steroid is added to the solvent, the latter already being at the reaction temperature.
7. A process of claim 1 wherein the solvent is biphenyl, diphenylene oxide, dibenzylbenzene, an oligoglycol dimethyl ether or a poly-$C_{4-8}$-alkanediol dimethyl ether.

* * * * *